United States Patent [19]

Rolla et al.

[11] Patent Number: 5,096,702

[45] Date of Patent: Mar. 17, 1992

[54] DENTIFRICE COMPOSITIONS

[75] Inventors: Gunnar Rolla, Oslo; Bjarne Svatun, Gjettum, both of Norway

[73] Assignee: Chesebrough-Pond's USA Co., Division of Conopco, Inc., Greenwich, Conn.

[21] Appl. No.: 580,883

[22] Filed: Sep. 11, 1990

[30] Foreign Application Priority Data

Sep. 14, 1989 [GB] United Kingdom ............... 8920796

[51] Int. Cl.⁵ ........................... A61K 7/16; A61K 7/18
[52] U.S. Cl. ......................................... 424/52; 424/57
[58] Field of Search ............................ 424/52, 57

[56] References Cited

U.S. PATENT DOCUMENTS

| 3,984,814 | 11/1976 | Cordon | 424/57 |
| 4,335,102 | 6/1982 | Nakashima et al. | 424/52 |
| 4,348,378 | 9/1982 | Kosti | 424/52 |
| 4,363,794 | 12/1982 | Ochal et al. | 424/52 |
| 4,459,277 | 7/1984 | Kosti | 424/49 |
| 4,522,806 | 6/1985 | Muhlemann et al. | 424/52 |
| 4,585,648 | 4/1986 | Maeyama et al. | 424/49 |
| 4,702,904 | 10/1987 | Maeyama et al. | 424/52 |
| 4,970,064 | 11/1990 | Adam et al. | 424/52 |

FOREIGN PATENT DOCUMENTS

| 0311260 | 4/1989 | European Pat. Off. . |
| 2462160 | 2/1981 | France . |
| 56-075422 | 6/1981 | Japan . |
| 845611 | 8/1960 | United Kingdom . |
| 2201593 | 1/1987 | United Kingdom . |

OTHER PUBLICATIONS

Nakashima et al, C.A.95:192230f (1981) 1 PR. 2462160 Feb. 13, 1981.

Lion Corp. CA.95:156375y (1981) of JP 56075422 Jun. 22, 1981.

Svatun, B. "Plaque-inhibiting effect of dentifrices containing stannous fluoride", (1978) pp. 205-210.

Svatun & Rolla, "The Role of Stannous Pyrophosphate in the plaque-inhibiting effect of dentifrices containing stannous fluoride",'Tooth surface interactions & preventive dentistry' (1981) pp. 33-37.

English Translation of Japanese Patent 56/45408 (Lion).

Primary Examiner—Shep K. Rose
Attorney, Agent, or Firm—Milton L. Honig

[57] ABSTRACT

The present invention relates to a dentifrice composition having an improved anti-plaque effect. The composition comprises stanous pyrophosphate as an anti-plaque agent, the activity of which can be increased according to the invention by including a water-soluble monofluorophosphate salt in the composition.

3 Claims, No Drawings

DENTIFRICE COMPOSITIONS

This invention relates to dentifrice compositions, more particularly to those having an anti-plaque effect, that is an ability to inhibit the growth of dental plaque.

Many compounds have been disclosed as having an anti-plaque activity. U.S. Pat. No. 4,522,806 (Muhlemann et al) includes a review of a large number of literature references concerning anti-plaque compositions ranging from those based on germicides such as cetylpyridinium chloride and chlorhexidine to those based on metal ions, such as stannous ions and zinc ions. The use of combinations of antibacterials and zinc salts is also referred to. The patent itself centres on the combination of hexetidine and a zinc salt.

Among the compounds that have been studied recently has been stannous fluoride and it has been shown that when applied as a mouthrinse it is effective in preventing plaque formation. However, when aqueous solutions are used, side effects such as a strong metallic taste and a yellowish-brown discolouration have been observed. Another study (Svatun, B. (1978) Acta. Odontol. Scand. 36 205-210) has shown that the plaque-inhibiting effect of stannous fluoride was maintained in a toothpaste containing 0.4% stannous fluoride and 1% stannous pyrophosphate whereas one containing the same amount of stannous fluoride but without stannous pyrophosphate exhibited no plaque-inhibiting property. A study to investigate the role of stannous pyrophosphate in toothpastes containing various relative amounts of stannous fluoride and stannous pyrophosphate has been reported by Svatun and Rolla, "The role of stannous pyrophosphate in the plaque-inhibiting effect of dentifrices containing stannous fluoride", 'Tooth Surface Interactions and Preventive Dentistry', IRL Press Ltd (London), pp 33 to 37, 1981. This study showed that there was a clear correlation between the content of stannous pyrophosphate and the plaque-inhibiting activity. The authors concluded that the role of stannous pyrophosphate in the plaque-inhibiting effect of dentifrices containing stannous fluoride conceivably is to be a reservoir of tin ions.

The present invention is based on certain further discoveries that have been made relating to dentifrices containing stannous pyrophosphate. It has now been discovered that the anti-plaque activity of a dentifrice containing stannous pyrophosphate can be enhanced by including a water-soluble monofluorophosphate, particularly sodium monofluorophosphate, in the dentifrice.

In dentifrices of this invention the amount of stannous pyrophosphate may range from 0.1 to 5% and the amount of monofluorophosphate salt may also range from 0.1 to 5%. Preferred ranges are 0.5 to 2% and 0.4 to 3%, respectively.

It is contemplated that in place of or in admixture with stannous pyrophosphate other sparingly soluble stannous compounds may be used, such as stannous metaphosphate, stannous oxide, stannous oxalate and stannous phosphate.

The dentifrice of the invention will contain usual additional ingredients in conventional amounts. Thus the dentifrice will usually comprise an abrasive cleaning agent, a liquid phase including an humectant, a binder or thickening agent, and a surfactant.

The preferred abrasive cleaning agent is alumina, especially alumina trihydrate (aluminium hydroxide). Other known abrasive agents that have been proposed for dentifrice use include silica, calcium pyrophosphate, calcium phosphate, insoluble sodium metaphosphate. The amount of the abrasive cleaning agent may range from about 10% to about 75% by weight of the dentifrice.

The liquid vehicle of the dentifrice may comprise water and a humectant typically in an amount of from about 10% to about 90% by weight of the dentifrice. Typical humectants are glycerol, sorbitol, propylene glycol and low molecular weight polypropylene and/or polyethylene glycols.

A wide variety of binders or thickening agents have been proposed for dentifrice use including sodium carboxymethyl cellulose, hydroxyethyl cellulose, hydroxyethylpropyl cellulose, xanthan gum, Irish moss, gum tragacanth, finely-divided silicas and synthetic hectorites. The amount of binder will usually range from about 0.5 to about 5% by weight of the dentifrice.

A further conventional ingredient of a dentifrice is an organic surfactant or mixture of surfactants. Many surfactants have been referred to in the literature but anionic surfactants are preferred because of their good foaming characteristics. Examples of anionic surfactants are the higher alkyl sulphates, especially sodium lauryl sulphate, and the alkyl aryl sulphonates, especially sodium dodecyl benzene sulphonate. Other examples are the substantially saturated higher aliphatic acyl amides of lower aliphatic amino carboxylic acid compounds, e.g. N-lauroyl sarcosine and alkali metal and alkanolamide salts thereof.

Various optional ingredients may be included in the dentifrice of the invention including flavouring agent, sweetening agent such as sodium saccharin, whitening agent such as titanium dioxide, preservative, other anti-plaque agents and/or antibacterial agents, anti-calculus agents, and agents for adjusting the dentifrice pH which may range from about 4 to about 8.

JP-A-56/45408 (Lion Dentifrice Co.) relates to compositions to be applied to the mouth comprising a sparingly soluble stannous compound, a soluble fluorine compound containing no tin ion, and a phytic acid compound. The phytic acid compound is said to enhance the solubility of the stannous compound, improve the stability of the dissolved stannous ion, increase the uptake of fluorine by the teeth, and result in an increase in the acid-resistance of tooth enamel. Example 3 of the publication gives the formula of a toothpaste comprising among other components, insoluble sodium metaphosphate (40%), stannous pyrophosphate (1.0%), sodium monofluorophosphate (0.76%) and pentasodium phytate (2.0%).

The following Examples illustrate the invention. Percentages are by weight.

EXAMPLE 1

A toothpaste having the following composition was made:

| Ingredient | % |
| --- | --- |
| Alumina trihydrate | 56.25 |
| Sorbitol syrup (70% solution) | 27.00 |
| Sodium lauryl sulphate | 1.50 |
| Xanthan gum | 0.875 |
| Stannous pyrophosphate | 1.00 |
| Sodium monofluorophosphate | 1.10 |
| Titanium dioxide | 0.50 |
| Sodium saccharin | 0.23 |
| Benzoic acid | 0.1875 |

| Ingredient | % |
| --- | --- |
| Flavour | 1.10 |
| Water | to 100.00 |

It was shown that this toothpaste had a substantially greater effectiveness in reducing the growth of dental plaque than a dentifrice from which the sodium monofluorophosphate was omitted but which was otherwise the same.

Clinical testing was conducted using the four-day non-brushing procedure described in the Svatun and Rolla publication referred to above which was published in "Tooth Surface Interactions and Preventative Dentistry". The toothpaste of this Example had a Plaque Index value of 0.23 whereas that of the comparative toothpaste not containing sodium monofluorophosphate had a Plaque Index value of 0.59.

In another test conducted in the same way the toothpaste of this Example had a Plaque Index value of 0.18.

EXAMPLE 2

A toothpaste having the following composition was made.

| Ingredient | % Example 2 |
| --- | --- |
| Alumina trihydrate | 56.25 |
| Sorbitol syrup (70% solution) | 27.00 |
| Sodium lauryl sulphate | 1.50 |
| Xanthan gum | 0.875 |
| Stannous pyrophosphate | 1.00 |
| Sodium monofluorophosphate | 1.10 |
| Titanium dioxide | 0.50 |
| Sodium saccharin | 0.23 |
| Benzoic acid | 0.1875 |
| Flavour | 1.10 |
| Triclosan[a] | 0.20 |
| Water | to 100 |

[a] 2,4,4'-trichloro-2'-hydroxy-diphenyl ether

The above toothpaste was effective in inhibiting the growth of dental plaque having a Plaque Index value of 0.10 in the test referred to in Example 1.

We claim:

1. A dentifrice composition having an improved anti-plaque effect consisting essentially of from 10-90% by weight of a liquid vehicle which comprises water and a humectant, from 10-75% by weight of an abrasive cleaning agent, from 0.1-5% by weight of stannous pyrophosphate and from 0.1-5% by weight of a fluorocompound, the composition being essentially free from a phytate salt, and wherein the fluorocompound is a water-soluble monofluorophosphate salt.

2. A composition according to claim 1, wherein the water-soluble monofluorophosphate salt is sodium monofluorophosphate.

3. A composition according to claim 1, comprising from 0.5-2% by weight of stannous pyrophosphate and 0.4-3% by weight of sodium monofluorophosphate.

* * * * *